United States Patent [19]

Ransohoff

[11] Patent Number: 5,112,492
[45] Date of Patent: May 12, 1992

[54] AUTOMATED BUBBLE TRAP

[75] Inventor: Thomas C. Ransohoff, Fairfield, Conn.

[73] Assignee: Biotage Inc., Charlottesville, Va.

[21] Appl. No.: 625,506

[22] Filed: Dec. 11, 1990

[51] Int. Cl.⁵ .................................. B01D 15/08
[52] U.S. Cl. ............................ 210/656; 210/129; 210/137; 210/143; 210/188; 210/198.2
[58] Field of Search ............... 210/635, 656, 659, 128, 210/129, 137, 143, 188, 198.2, 750, 85, 87, 90, 96.1; 73/61.1 C; 422/70; 436/161

[56] References Cited

U.S. PATENT DOCUMENTS

| | | | |
|---|---|---|---|
| 3,701,609 | 10/1972 | Bailey | 210/198.2 |
| 3,830,369 | 8/1974 | Pfadenhauer | 210/198.2 |
| 3,946,731 | 3/1976 | Lichenstein | 210/87 |
| 4,116,046 | 9/1978 | Stein | 210/198.2 |
| 4,117,727 | 10/1978 | Friswell | 73/61.1 C |
| 4,153,554 | 5/1979 | Von Der Heide | 210/96.2 |
| 4,385,357 | 5/1983 | Davis | 210/143 |
| 4,568,465 | 2/1986 | Davis | 210/143 |
| 4,743,373 | 5/1988 | Rai | 210/198.2 |
| 4,840,730 | 6/1989 | Saxena | 210/96.1 |
| 4,842,730 | 6/1989 | James | 210/198.2 |
| 4,891,133 | 1/1990 | Colvin | 210/198.2 |
| 4,897,184 | 1/1990 | Shouldice | 210/87 |
| 4,911,703 | 3/1990 | Lysaght | 604/28 |
| 4,981,597 | 1/1991 | Allington | 210/198.2 |

Primary Examiner—Ernest G. Therkorn
Attorney, Agent, or Firm—Sheldon H. Parker

[57] ABSTRACT

An automated bubble trap for a liquid chromatography system includes a bubble trap or reservoir with level sensing devices at spaced elevations so that the liquid chromatography system can be operated unattended on a day to day basis so long as the liquid level is maintained between the liquid sensing elevations. The automated bubble trap will correct a low level condition restoring the liquid level to proper limits. However if a dry line condition is inferred, then the automated bubble trap will shut down the system until the problem is resolved.

2 Claims, 2 Drawing Sheets

AUTOMATED BUBBLE TRAP

BACKGROUND OF THE INVENTION

The present invention is directed to liquid chromatography and is particularly concerned with an automatic arrangement for trapping and removing air from a liquid chromatography feed system.

In liquid chromatography a liquid sample is passed by a flowing stream of liquid solvent (the mobile phase) through a column packed with particulate matter (stationary phase). While passing through the column the various components in the sample separate from one another by adsorbing and desorbing from the stationary phase at different rates such that these individual components elute from the column at different times. The separated components then flow through a detector which responds to each component both qualitatively and quantitatively thereby providing information to the user about the separation achieved by the chromatography column.

The particulate matter in the chromatography column is generally referred to as the chromatography media and the resolution of a separation of the stream into individual components by the chromatography media is a primary measure determinant of the economic value of the chromatography.

Accordingly it is necessary to protect the chromatography media from conditions which will ruin the media including the presence of air and the presence of microbial contamination.

The presence of air in a chromatography column fills the pores of the chromatography media and blocks the liquid sample from getting to the active sites of the media. Additionally the presence of air disrupts the flow of the liquid sample as it is essential to achieve even flow of the liquid sample through the column.

Microbial or bacterial contamination is a particular problem with low pressure chromatography in that the liquid phase is aqueous and the gel media a carbohydrate. With water present bacteria can grow interfering with the ability of the media to produce a clean, pure product.

Accordingly it is highly desirable to prevent air from entering the column and to provide a bubble trap that not only excludes air from entering the column but also is of sanitary design to inhibit the growth of bacteria within the chromatography system and, in particular the chromatography column. Bubble traps are a known technique in liquid chromatography for protecting the chromatography column and more specifically the chromatography media. A typical bubble trap comprises a reservoir located at the down stream end of a system pump for delivering a liquid to a chromatography column. The reservoir supplies the liquid to the chromatography column. Any air whether from air entrapped in the liquid, or resulting from a slow leak, or from a dry line condition would be trapped in the upper portion of the reservoir above the level of the liquid therein.

Heretofore bubble traps have not been automated or have been minimally automated. The result is that during unattended operation common in liquid chromatography processes (some reaching days in duration) in the event of depletion of liquid in the bubble trap, air will eventually reach the liquid chromatography column. This problem can be minimized by increasing the bubble trap holding volume; however, this also increases the difficulty of cleaning the bubble trap, already a major concern in the biopharmceutical industry and increases system holdup volume which degrades the system effectiveness in achieving the desired separation of the mixture being processed.

SUMMARY OF THE INVENTION

The present invention provides a bubble trap that enables trouble free unattended operation by combining automation, low holdup volume and sanitary design. The bubble trap may be positioned in a liquid chromatography system at the down stream end of the system pump and upstream of the chromatography column. The bubble trap functions as a reservoir for receiving the entire volume output of the system pump. The reservoir is preferably though not necessarily transparent being made of glass or polysulfone for example and includes level detection devices at spaced elevations in the reservoir for the purpose of maintaining the liquid sample between the two elevations. This is accomplished by refilling the trap in the event the liquid sample level falls below the first or lower level or closing down the chromatography system in the event the liquid level fails to rise above the higher or second level within a predetermined time period during refilling. The latter condition is indicative of a dry line condition in which the system pump is now pumping air into the reservoir.

For some operations, as for example, loading the sample into the column the automated bubble trap may be temporarily bypassed.

OBJECTS OF THE INVENTION

It is an object of the invention to provide an automated bubble trap for a liquid chromatography system.

It is another object of the present invention to provide an automated bubble trap which accommodates unattended multiday operation of a liquid chromatography system.

Another object of the invention is to provide an automated bubble trap of sanitary design inhibiting the condition of bacterial contamination of the chromatography column.

Another object of the invention is to provide a practical low hold up volume bubble trap which minimizes the impact of the trap on separation resolution.

Other and further objects of the invention will occur to those skilled in the art on employment of the invention in practice or with a full understanding of the following detailed description of the invention.

DESCRIPTION OF THE DRAWING

A preferred embodiment of the invention has been chosen for purposes of description and illustration and is shown in the accompanying drawing in which.

Figure 1:
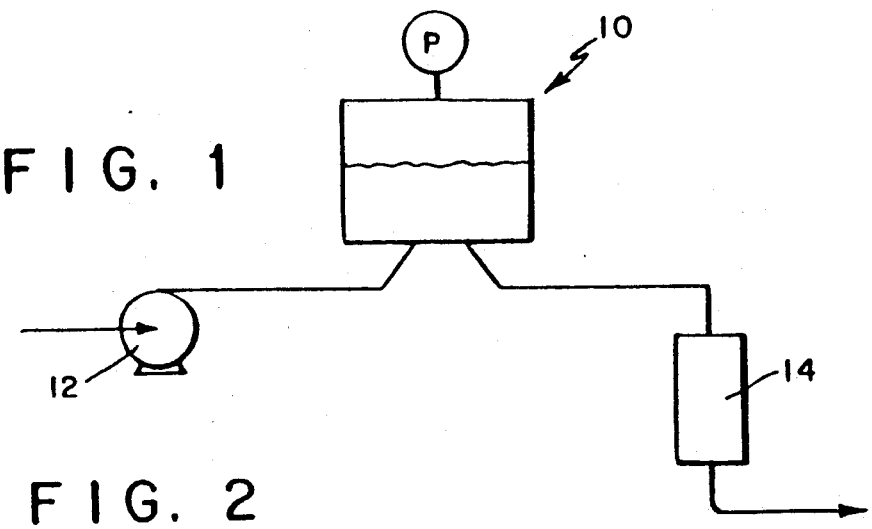
FIG. 1 is a simplified flow path of a portion of a liquid chromatography system including a system pump, bubble trap and a chromatography column.

Referring now to the drawing, FIG. 1, the automated bubble trap 10 of the invention is typically placed between a system pump 12 and a liquid chromatography column 14.

Figure 2:
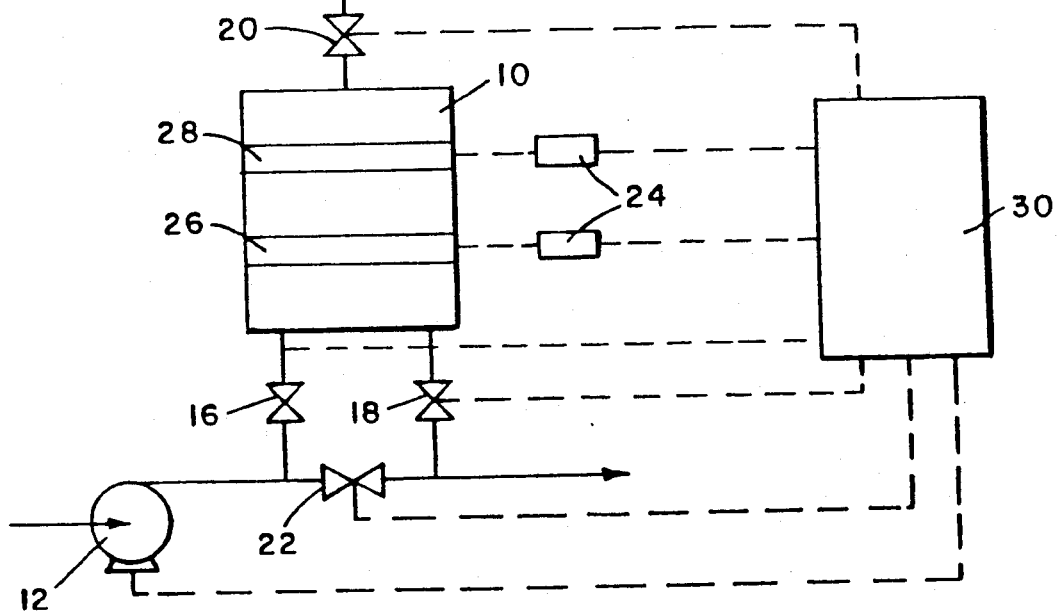
FIG. 2 is a schematic view of an automated bubble detector according to the present invention.

The bubble trap 10 (FIG. 2) functions as a reservoir and is provided with inlet 16 and outlet 18 valves and a top exhaust valve. The inlet and outlet valves are normally opened during operation while the exhaust valve is normally closed. A bypass valve 22 may be located between the inlet and outlet valves to the bubble trap so that the bubble trap can be bypassed for certain operations such as sample loading of the liquid column.

The bubble trap comprises a reservoir 10 of suitable construction and is generally tubular and preferably fabricated of transparent material such as glass. Other materials suitable for sanitary design may be used such as Teflon, polysulfone, stainless steel, etc. The bubble trap is fitted with level sensing means 24 such as optical detectors for detecting liquid sample levels at spaced elevations in the bubble trap designated as lower and upper levels 26, 28. The level sensors can be of known construction operating on capacitance, mechanical, ultrasonic or optical principles. The operation of the bubble trap is controlled by a controller 30 which receives inputs from the level sensors and sets the valves on the automated bubble trap according to the controller design. The valves may be diaphragm valves, can be of sanitary design and may be constructed of stainless steel, polypropylene, Teflon, polyvinylidenedifluoride (PVDF) or some other material of suitable construction.

During normal operation, the bubble trap controls the level of the liquid between the lower and upper sensing levels and will shut down the operation in the event the liquid level can not be maintained between these two elevations.

During normal operation, the bubble trap will have inlet and outlet valves open. If the liquid level falls below the lower elevation, the system infers that air is being detected at the lower elevation, the outlet valve will close and the exhaust valve will open until the liquid level rises and it is detected at the upper elevation. If upper level detection of liquid does not occur within a preset time period, which will be dependent on the refill flow rate and on the bubble trap volume, then the system will shut down because a dry inlet line condition is inferred and the condition must be corrected before continuing operation.

The bubble trap may be automatically bypassed—for example during column loading—with inlet and outlet valves closed and with the bypass valve opened. For filling of the bubble trap the liquid inlet valve and exhaust valve will be open, and the outlet valve closed. For draining the bubble trap the inlet valve is closed and the exhaust and outlet valves are opened. For sanitary purposes the bubble trap can be thoroughly cleaned using a preprogrammed procedure. For example, the bubble trap would be filled as described above with a cleaning solution until liquid is sensed at the upper level sensor, and then for an extra period of time to ensure that the exhaust valve is cleaned. This filling operation may be followed by a soak period, then by a draining operation, and then by refilling with the operating solvent or buffer. In the preferred embodiment, the controller is a programmable logic controller (PLC). It may also be a specialized controller, a personal computer, or any controller capable of handling the inlet/outlet, timers, and logic required.

Figure 3:
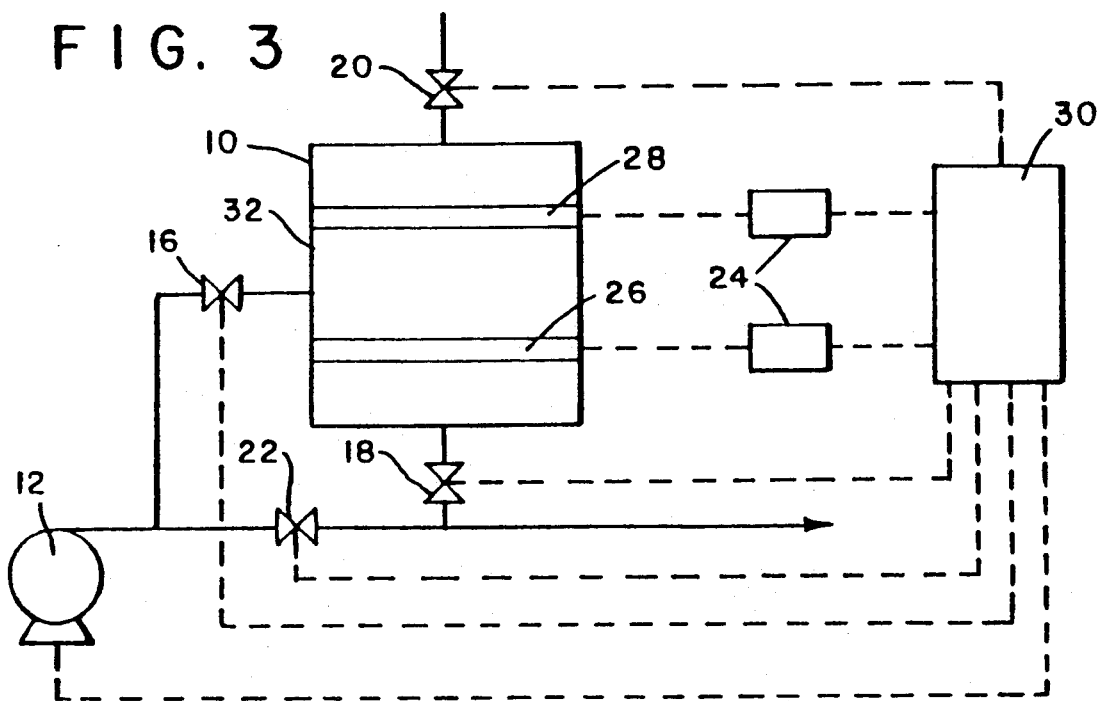
FIG. 3 is a modification of the bubble trap of FIG. 2.

There are several modifications of the automated bubble trap including location of the inlet valve through the side wall 32 of the reservoir (FIG. 3) which provides better mixing of the liquid sample in the bubble trap as well as better cleaning.

Figure 4:
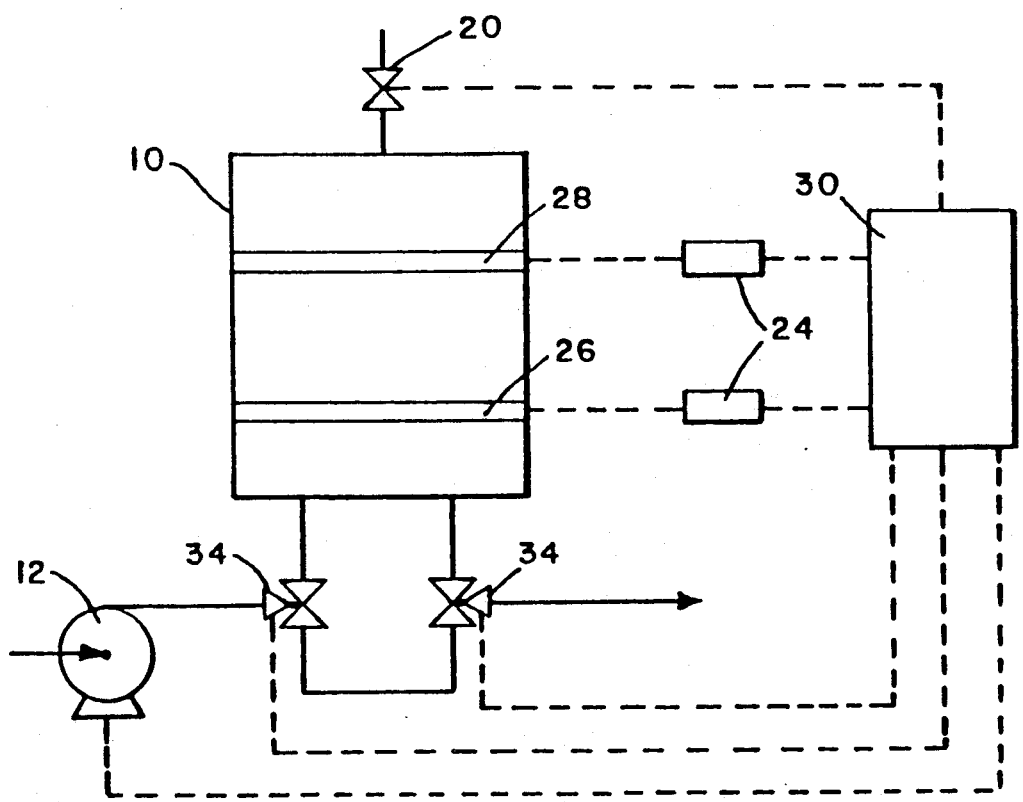
FIG. 4 is another modification of the bubble trap of FIG. 2.

In another modification shown in FIG. 4, the inlet, outlet, and bypass valves may be replaced by two three-way valves 34 so that the inlet, outlet, and bypass functions indicated above can be readily accomplished with two valves.

In a further modification the liquid level sensor at the upper elevation can be omitted. In this modification, when air is detected at the lower elevation, the pump will refill the bubble trap with liquid sample for a given time, dependent on the fill flow rate and bubble trap volume. If air is still detected at the lower elevation after the time elapsed for refill, then a dry line condition is inferred and the system will be shut down.

Figure 5:
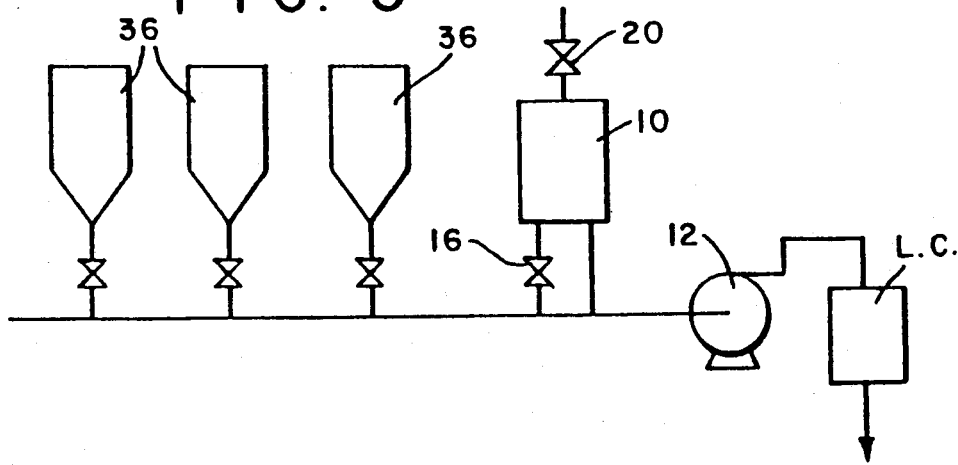
FIG. 5 is another modification of a bubble trap of the invention.

In a further modification shown in FIG. 5, the bubble trap 10 may be placed between the inlet tanks 36 (which are preferably pressurized) and the system pump 12. This is particularly useful for high pressure liquid chromatography (HPLC) applications where pressures downstream of the pump typically range from 500 to 2000 psig prohibiting the use of glass or plastic bubble traps. It is also useful in situations where introduction of air can damage or impair the performance of the pump. In this modification the exhaust is selectively and preferably under vacuum.

A primary advantage of the automated bubble trap is that it allows use of a smaller and lower hold up or reservoir volume bubble trap. Because of the automated nature of the design a bubble trap so small as to require constant attention is now possible. This represents an enormous advantage in low pressure liquid chromatography operations where resolution and cleanliness are primary concerns.

Having thus described the invention, I claim:

1. An automated method of trapping air in a liquid chromatography system comprising the steps of supplying a liquid to a liquid chromatography column via a reservoir, maintaining the level of the liquid in the reservoir between lower and upper elevations, automatically interrupting the supply of liquid to the column in the event the liquid level falls below the lower elevation, supplying liquid to the reservoir, and automatically restoring the supply of liquid to the column in the event the liquid level reaches the upper elevation within a predetermined elapsed time.

2. A method according to claim 1 which includes the step of shutting down the liquid chromatography system in the event the liquid sample level does not reach the upper elevation during the predetermined time elapsed.

* * * * *